(12) United States Patent
Huang

(10) Patent No.: US 10,130,425 B2
(45) Date of Patent: Nov. 20, 2018

(54) METHOD AND SYSTEM FOR SKIN BLEMISHES LAYERED SKIN TREATMENT

(71) Applicant: Po-Han Huang, Kaohsiung (TW)

(72) Inventor: Po-Han Huang, Kaohsiung (TW)

( * ) Notice: Subject to any disclaimer, the term of this patent is extended or adjusted under 35 U.S.C. 154(b) by 163 days.

(21) Appl. No.: 14/816,330

(22) Filed: Aug. 3, 2015

(65) Prior Publication Data

US 2017/0035507 A1 Feb. 9, 2017

(51) Int. Cl.
*A61B 18/20* (2006.01)
*A61B 18/00* (2006.01)

(52) U.S. Cl.
CPC .... *A61B 18/203* (2013.01); *A61B 2018/0047* (2013.01)

(58) Field of Classification Search
CPC .................................................... A61B 18/203
USPC ......................................... 606/9, 3; 128/898
See application file for complete search history.

(56) References Cited

U.S. PATENT DOCUMENTS

| 6,916,328 | B2* | 7/2005 | Brett | A61B 17/3403 606/167 |
|---|---|---|---|---|
| 9,358,064 | B2* | 6/2016 | Clark, III | A61B 18/14 |
| 2003/0130628 | A1* | 7/2003 | Duffy | A61B 17/22 604/289 |
| 2006/0116669 | A1* | 6/2006 | Dolleris | A61B 18/203 606/17 |
| 2006/0241673 | A1* | 10/2006 | Zadini | A61B 17/0218 606/192 |
| 2007/0060989 | A1* | 3/2007 | Deem | A61B 18/1477 607/99 |
| 2007/0260229 | A1* | 11/2007 | Navarro | A61B 18/203 606/9 |
| 2008/0039826 | A1* | 2/2008 | Scheibner | A61B 18/203 606/9 |
| 2011/0028898 | A1* | 2/2011 | Clark, III | A61B 18/1477 604/151 |

* cited by examiner

*Primary Examiner* — Ahmed Farah
(74) *Attorney, Agent, or Firm* — WPAT, PC

(57) ABSTRACT

A system and method for performing layer treatment for skin blemish in which the target area of the skin is first treated by performing a deep layer treatment by cutting the fibrous bands and then performing a superficial skin treatment by using electromagnetic radiation and both of the treatment take place within the same day.

2 Claims, 8 Drawing Sheets

METHOD AND SYSTEM FOR SKIN BLEMISHES LAYERED SKIN TREATMENT

BACKGROUND OF THE INVENTION

Field of the Invention

This invention relates to a method and system for skin treatment. It specifically refers to a layered skin treatment. The present invention relates to methods and system of dermatological treatment that involve performing a deep layer treatment by cutting the fibrous bands under the skin of target area and performing electromagnetic radiation on the target area within one day.

Background Art

Skin is made up of two layers, the outer layer, epidermis, and the deeper layer called the dermis. The main structural component of the dermis is collagen protein, which provides the skin with the flexibility and strength of the skin. Skin been the largest organ in human body, protect the body from injuring the internal organs, is exposed to environment pollutants and UV ray, thus, likely to cause undesirable conditions such as wrinkles; acne, excessive sebum (oil) production, enlarged pores; sun damage; actinic keratoses; actinic chelitis; acne vulgaris; brown spots such as age-spots and freckles; hyper- and hypo-pigmentation, excessive sebum (oil) production, sebaceous hyperplasia (enlarged oil glands) and pigmented lesions, such as scars.

Treatments have been developed to improve or restore the condition of the skin, mostly seen in the dermis. Prior inventions such as electromagnetic radiation treatment has been used to treat patients with scars, aging and wrinkles. In addition global scarring grading system is used to assist physicians to evaluate the condition of the skin. Grade 1 refers to flat marks visible to patients or observer irrespective of distance and it is shown with red, hyper or hypo-pigmented flat macules. Grade 2 refers to mild atrophy or hypertrophy which is not obvious at social distances (≥50 cm) or may be covered adequately by makeup and it generally have mild rolling small and soft papular. Grade 3 refers to moderate atrophy or hypertrophy which is obvious at social distances (≥50 cm) and it does not covered easily by makeup, however, it is still able to be flattened by manual stretching. Lastly, grade 4, is a severe atrophy or hypertrophy which is obvious at social distances (≥50 cm) and is not able to be flattened by manual stretching. Examples of Grade 4 condition skin include gross atrophy, dystrophic scars and significant hypertrophy or keloid.

Moreover, invasive treatment that involve cutting or repairing the skin deeper layer are invented as well. However, the existing treatments have limited recovery rate and also the entire length of treatment may be long due to time interval between each treatment. Thus, patient may prefer treatment that can achieve higher skin recovery rate without have to wait for next treatment.

In summary, it would be desirable to combine the electromagnetic radiation therapy with dermatological therapies such as cutting of fibrous bands, however, in a specific sequence and both steps are to be performed in the same day, to enable the patent to experience less pain, better recovery and heal in a shorter period of time. This can be extremely useful when compare with procedures that may require multiple treatments and lower the restore rate of the skin conditions.

SUMMARY OF THE INVENTION

One aspect of the invention is to provide a layered treatment method for skin blemishes. It comprises deep and superficial skin procedures. The deep procedure treats the irregular fibrosis and tissue contracture of dermis and sub-cutis and the superficial procedure treats the roughness of epidermis and dermis. The aforementioned methods can smoothen the superficial skin and restore the skin condition. More importantly, the claimed layered skin treatment method can reduce dependence on monotherapy and produce shorten recovery time as well as improving the treatment efficacy.

To achieve the above objective, the invention provides a layered treatment for skin blemishes. It comprises the deep layer treatment by cutting fibrous bands over 1 mm beneath the surface of target skin area with a surgical needle followed by performing a superficial layer treatment by irradiating skin cells within 1 mm beneath the target area with electromagnetic radiation. Unexpected improvement of skin condition is shown.

In one embodiment, the treatment comprises administering at least one substance to the aforementioned target area, in which the substance is among the following groups: growth factor, collagen by-product, collagen precursor, hyaluronic acid, vitamin, antioxidant, amino acids, supplemental minerals, platelet-rich plasma, skin-whitening medication or ingredient and any combinations thereof.

In another embodiment, before performing the layered treatment, a pre-treatment image of target area is taken by image device and later compared with post treatment image with comparative image analysis device.

In one embodiment, a therapeutically effective amount of electromagnetic radiation is administered to treat at least one dermatological pathology selected from the following groups: inflammatory skin condition, acne, skin aging, loose skin, irregular skin texture, enlarged pores, scars, pigment changes, wrinkles, atrophic skin disease, congenital skin defect and any combinations thereof.

In one embodiment, electromagnetic radiation source is selected among the following groups: the carbon dioxide laser, Er:YAG laser, fractional CO2 laser, Er:YAG Fraxel laser, Fractional RF, Fraxel laser, 1550 nm and any combinations thereof.

In one embodiment, the electromagnetic radiation source has an energy transfer rate of r. The range of r is between 0.0013 $J/cm^2/sec$ and 0.02 $J/cm^2/sec$.

In one embodiment, the electromagnetic radiation has a wavelength that ranges from 9400 nm to 111000 nm.

In one embodiment, the deep layer treatment is followed by the superficial treatment and both treatments are completed in the one day.

Another aspect of the present disclosure provides skin blemishes treatment system which comprises a subcision device like surgical needle, cutting fibrous bands over 1 mm beneath the target area with a surgical needle, and the electromagnetic radiation source, irradiating skin cells within 1 mm beneath the target area with electromagnetic radiation.

In one embodiment, the skin blemish treatment system comprises administering at least one substance to the target skin area, in which the substance is selected among the following the group: growth factor, collagen by-product, collagen precursor, hyaluronic acid, vitamin, antioxidant, amino acids, supplemental minerals, platelet-rich plasma, skin-whitening medication or ingredient and any combinations thereof.

In another embodiment, the skin blemish treatment system comprises an imaging device and a comparative image analysis device in which before performing the layered treatment, a pre-treatment image of target area is taken by image device and later compared with post treatment image with comparative image analysis device.

In one embodiment, the skin blemish treatment system comprises administering a therapeutically effective amount of electromagnetic radiation to at least one dermatological pathology selected from the following groups: inflammatory skin condition, acne, skin aging, loose skin, irregular skin texture, enlarged pores, scars, pigment changes, wrinkles, atrophic skin disease, congenital skin defect and any combinations thereof.

In one embodiment, the skin blemish treatment system comprises an electromagnetic radiation source that is selected among the following groups: the carbon dioxide laser, Er:YAG laser, fractional CO2 laser, Er:YAG Fraxel laser, Fractional RF, 1550 nm Fraxel laser and any combinations thereof.

In one embodiment, the skin blemish treatment system comprises an electromagnetic radiation source that has an energy transfer rate of r. The range of r is between 0.0013 $J/cm^2/sec$ and 0.02 $J/cm^2/sec$.

In one embodiment, the skin blemish treatment system comprises an electromagnetic radiation that has a wavelength that ranges from 9400 nm to 111000 mn.

In one embodiment, the skin blemish treatment system comprises deep layer treatment follow by the superficial treatment and both treatment are completed within the same day.

In summary, unexpected result is produced by a deep skin layer treatment followed by a superficial skin layer treatment and both treatment must occur within one day.

BRIEF DESCRIPTION OF THE DRAWINGS

The present invention can be more fully understood by reading the following detailed description of the preferred embodiments, with reference made to the accompanying drawings, wherein.

DETAILED DESCRIPTION OF THE INVENTION

Figure 1A:
FIGS. 1A-1B are diagrams showing the comparison between before FIG. 1A and after layered treatment FIG. 1B.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Method of Treating Skin Blemishes

The present disclosure provides a layered treatment for skin blemishes for patients. Unexpected result is produced by a deep skin layer treatment followed by a superficial skin layer treatment and both treatment must occur within one day. The first aspect for the present invention provides a layered treatment for skin blemishes. It comprises two procedures. The first is a deep skin layer treatment and followed by a superficial skin treatment. The deep skin layer treatment cuts fibrous bands over 1 mm beneath the target surface area with a surgical needle.

The aforementioned deep skin layer treatment refers to subcision in which it uses a needle tip to remove connective tissue under the scar, causing blood clots and swelling, and healing the dent through post-injury fibrosis. The surgical needle can be a sharp or blunt needle of 30 G, 27 G, 25 G, 22 G, 18 G, etc. The outer and inner diameters of said needle are 0.4 mm and 0.2 mm respectively. The superficial treatment irradiates skin cells within 1 mm beneath the target surface area with electromagnetic radiation.

In the preferred embodiment, the layered treatment for skin blemishes further comprises administering of at least one substance into the target area. The option of the aforementioned substance is among the following groups: growth factor, collagen by-product, collagen precursor, hyaluronic acid, vitamin, antioxidant, amino acids, supplemental minerals, platelet-rich plasma, skin-lightening medication or ingredient and any combinations thereof. Administration of a substance refers to filling by injection or fat grafting. Filling by injection mainly refers to injecting supportive collagen and hyaluronic acid under the depressed dermis so as to restore the elasticity of the skin.

In the preferred embodiment, the layered treatment for skin blemishes further comprises an analytic procedure. Before undergoing the aforementioned layered treatment for skin blemishes, the pre-treatment picture of the target area is taken with an image-capturing device, and the post-treatment picture of the target area is taken with the same image-capturing device. The pre-treatment picture is compared with the post-treatment for reference. The image capturing device is a 14-megapixel Canon camera. Pictures are taken under normal, polarized and ultraviolet lights. Areas of depressed skin before and after treatment are measured and compared by using a comparative image analysis device. The aforementioned analysis is done with JANUS II Facial Imaging System (PSI Co, Korea). Pictures are analyzed with image software for pores, wrinkles, skin color, UV damage, pigmentation and sebum secretion.

In the preferred embodiment, the skin blemish system treats at least one dermatological pathology that is selected from the following groups: inflammatory skin condition, acne, skin aging, loose skin, irregular skin texture, enlarged pores, scars, pigment changes, wrinkles, atrophic skin disease, congenital skin defect and any combinations thereof.

In the preferred embodiment, the skin blemish the superficial skin treatment refers to electromagnetic radiation-mediated erosion, removal, destruction, damage or irritation of multiple small irradiated areas (less than 1 mm) as a therapy for skin improvement. The irradiated area can be oval, round, arched or a straight line in shape. The electromagnetic radiation source is among the following groups: the carbon dioxide laser, Er:YAG laser, fractional CO2 laser, Er:YAG Fraxel laser, Fractional RF, 1550 nm Fraxel laser and any combinations thereof. In the preferred embodiment, the electromagnetic radiation source has an energy transfer rate of r. The range of r is between 0.0013 /cm²/sec and 0.02 J/cm²/sec. In the preferred embodiment, the electromagnetic radiation source has an energy density range between 2.5 J/cm² and 20 J/cm². In the preferred embodiment, the electromagnetic radiation has a wavelength that ranges from 9400 nm to 111000 nm. In the preferred embodiment, the deep layer treatment take place first, then the superficial layer treatment, and both layer treatment must be performed within one day.

The second aspect for the present invention provides a layered treatment system for skin blemishes. It consists of subcision and electromagnetic radiation devices. The aforementioned subcision device cuts fibrous bands over 1 mm beneath the target surface area with a surgical needle.

The electromagnetic radiation device irradiates skin cells within 1 mm beneath the target area with electromagnetic radiation. The aforementioned subcision uses a sharp needle or blunt needle of 30 G, 27 G, 25 G, 22 G, 18 G, etc. The outer and inner diameters of said needle are 0.4 mm and 0.2 mm respectively. The needle tip removes connective tissue under the scar, causing blood clots, swelling, and heals the dent through post-injury fibrosis.

In the preferred embodiment, the layered treatment system for skin blemishes further comprises administering at least one of the substances into the target area. The substance is among the following groups: growth factor, collagen by-product, collagen precursor, hyaluronic acid, vitamin, antioxidant, amino acids, supplemental minerals, platelet-rich plasma, skin-whitening ingredient and any combinations thereof. Administration of a substance refers to filling by injection or fat grafting. Filling by injection mainly refers to injecting supportive collagen and hyaluronic acid under the depressed dermis so as to restore the elasticity of the skin.

In the preferred embodiment, the layered treatment system for skin blemishes further comprises the image-capturing procedure. Before undergoing the aforementioned layered treatment for skin blemishes, the pre-treatment picture of the target area is taken with an image-capturing device, and the post-treatment picture of the target area is taken with the same image-capturing device. The pre-treatment picture is compared with the post-treatment one for reference. The analysis is done with JANUS II Facial Imaging System (PSI Co, Korea). The image capturing device is a 14-megapixel Canon camera. Pictures are taken under normal, polarized and ultraviolet lights. Areas of skin pits before and after treatment are measured and compared. Pictures are analyzed with image software for pores, wrinkles, skin color, UV damage, pigmentation and sebum secretion. In the preferred embodiment, the skin blemish system treats at least one dermatological pathology selected among the following groups: inflammatory skin condition, acne, skin aging, loose skin, irregular skin texture, enlarged pores, scars, pigment changes, wrinkles, atrophic skin disease, congenital skin defect and any combinations thereof.

In the preferred embodiment, the skin skirmish treatment system uses electromagnetic radiation source among the following groups: the carbon dioxide laser, Er:YAG laser, fractional CO2 laser, Er:YAG Fraxel laser, Fractional RF, 1550 nm Fraxel laser and any combinations thereof. In the preferred embodiment the skin skirmish treatment system uses electromagnetic radiation source that has an energy transfer rate of r. The range of r is between 0.0013 J/cm²/sec and 0.02 J/cm²/sec. In the preferred embodiment, the skin skirmish treatment system uses an electromagnetic radiation source has an energy density that range between 2.5 J/cm² and 20 J/cm². In the preferred embodiment, the skin skirmish treatment system uses electromagnetic radiation has a wavelength that ranges from 9400 nm to 111000 nm.

The result of skin improvement is imageologically and objectively evaluated with JANUS II Facial Imaging System (PSI Co, Korea). The 14 megapixel Canon camera captures images under normal, polarized and ultraviolet lights. Taken images are analyzed for pores, wrinkles, skin color, UV damage, pigmentation and and sebum secretion.

Definitions

Articles "a" and "an" are used herein to refer to one or to more than one (i.e. at least one) of the grammatical object of the article.

Unless otherwise defined, all technical terms used herein have the same meaning as commonly understood by one of ordinary skill in the art to which this disclosure belongs.

The term used herein "skin blemish" refers to any skin lesion, scar originating from (but not limited to) cosmetic breast implant surgery, back, central chest, heart region, abdomen, caesarean section, pubic area and joint surgeries, burns, aging, and photoaging, or wrinldes.

The term "scar" herein refers to any skin anomaly on all parts of the body owing to the formation of fibrous tissue (fibrosis) or sclerosis (for example, scleroderma), or damage on normal skin component owing to surgical procedures, trauma, burns, radiation, chemical exposure, or disease (including infection). Scar types include (but are not limited to) hypertrophic scars, sunken scars, and stretch marks. When the body produces too much collagen, it results in hypertrophic scars, bulging over the surrounding skin. One type of hypertrophic scars is the keloid scar, which includes regenerated keloid scar after the excision of the previous one. An atrophic or depressed scar is concave in appearance, and caused by the loss of the skin's underlying supporting structure. When the skin is rapidly stretched (ex. due to the significant weight gain or growth spurt), or healed under tension (usually near the joints), it generates stretch marks (striae).

The term "wrinkle" herein refers to the ridges, creases, dents, pits, or recessed areas caused by habitual facial expressions and loss of collagen and/or elasticity due to aging, sunburn, smoking, poor hydration, and various other factors. Wrinkles range from creases to fine lines. Wrinkles appear in any part of the body. In this context, wrinldes refer to the wrinkles on the head and neck. The treatable wrinkles for the present invention include (but are not limited to) forehead wrinkles, crow's feet, nasolabial folds, single or multiple fine lines around the eyes or brows and combinations thereof.

The term "treatment" herein refers to temporary or permanent prevention and alleviation (or elimination) of single or multiple skin blemishes. It means the dimensions (length, width, height or depth), characteristics, color or texture of treated skin blemishes are restored to those of normal tissues. In this regard, the aforementioned layered treatment can reduce or slow down scar formation.

The term "subcision device" herein refers to a dermatological device for subcision of sub-epidermic tissues. The device includes a blunt dermis contacting surface which allows the physician to lift or cause traction to the skin from underneath the skin. Placement of the dermal contacting surface of the device under the skin is achieved by penetrating the skin of a patient via a sharp tip within the device. By mere skin lifting from underneath, fibrous bands present within the dermis are detached/disrupted/dissected from their attachments to the skin or from their attachments to deeper layers.

The term "one day" herein refers is equivalent to the same day which is limits to a duration of 24 hours or less.

The term "growth hormone" herein refers to the secretion from the pituitary gland that causes growth of all tissues of the body that are capable of growing.

The term "vitamin" herein refers to an organic compound which organism cannot synthesize and a vital nutrient that an organism requires in limited amount. This can be achieved obtained through the diet. In addition, the term "vitamin" is conditional upon the circumstances and the particular organism.

The term "therapeutic effective amount" herein refers to an amount of a subject active high enough to provide a significant positive modification of the condition to be treated. A therapeutic effective amount of the subject active will vary with the particular condition being treated, the severity of the condition, the duration of the treatment, the nature of concurrent treatment, and like factors.

The term "skin atrophy" herein refers to the thinning and/or general degradation of the dermis often characterized by a decrease in collagen and/or elastin as well as decreased number, size and doubling potential of fibroblast cells. Skin atrophy is a natural result of aging. Skin atrophy may be caused by either intrinsic or extrinsic factors such as natural chronoaging, photodamage, burns, or chemical damage. Skin atrophy is often an undesirable side effect resulting from treatment with corticosteroids.

The following examples will further illustrate the present invention of a method and system for the layered treatment for skin blemishes. The following examples are merely exemplary. It should not be used to limit the scope of the invention. Skilled professionals can make adjustments and modifications based on the manual of this invention or their general knowledge in this field and still remain in line with the scope of the present invention.

EXAMPLE 1

Comparison of Monotherapy with Claimed Layered Skin Treatment

Figure 2A:
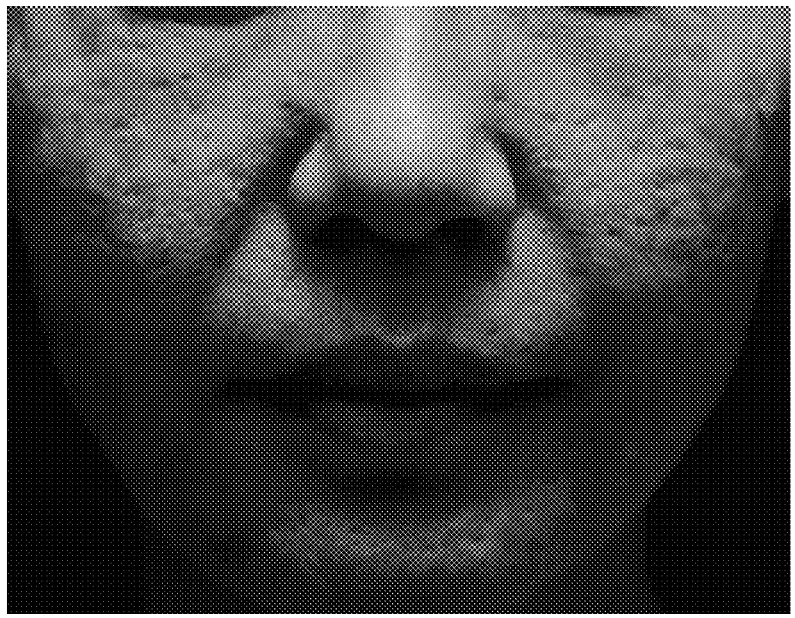
FIGS. 2A-2B are diagrams showing the comparison between before FIG. 2A and after carbon dioxide Fraxel laser treatment FIG. 2B.
Figure 2B:
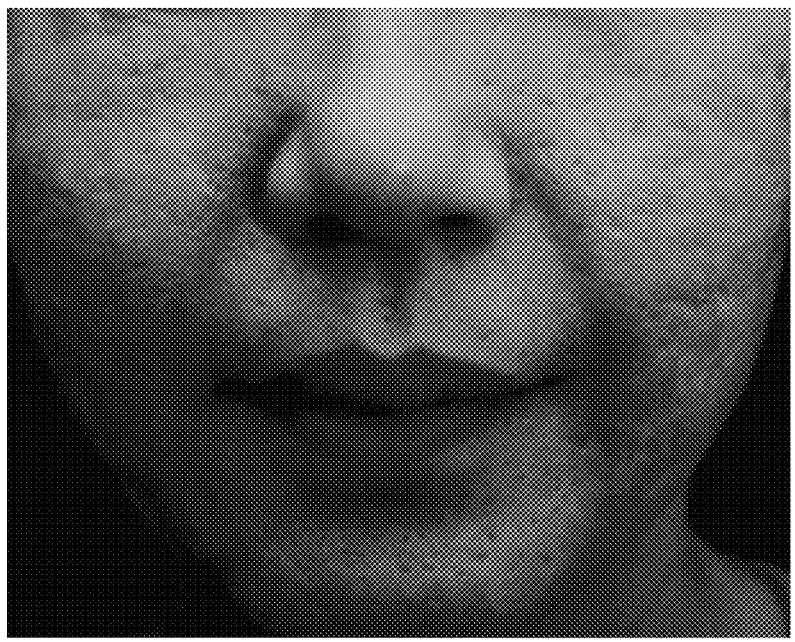

FIGS. 2 depicts the patient treated with only carbon dioxide Fraxel laser. FIG. 2A depicts pre-treatment skin. FIG. 2B depicts post-treatment skin. In general, if the skin scar is a moderate scar, carbon dioxide Fraxel laser alone can improve the skin condition by 10-20%, however, if it is a severe scar, then, carbon dioxide Fraxel laser alone produces no visible effect.

Figure 3A:
FIGS. 3A-3B are diagrams showing the comparison between before FIG. 3A and after subcision alone FIG. 3B.
Figure 3B:

FIGS. 3 depicts the patient treated with only subcision. FIG. 3A depicts pre-treatment skin. FIG. 3B depicts post-treatment skin. If the skin scar is a moderate-to-severe scar, subcision alone only improves the skin condition by 20%.

Figure 1B:

FIG. 1 depicts the patient treated with the present invention of layered treatment for skin blemishes. The treatment comprises subcision on deep skin and carbon dioxide Fraxel laser on superficial skin. FIG. 1A depicts pre-treatment skin. FIG. 1B depicts post-treatment skin. The result shows that the layered skin treatment improves skin condition by 40-50%. The result shows that layered skin treatment has a better effect than either carbon dioxide Fraxel laser or subcison alone.

EXAMPLE 2

Figure 4A:
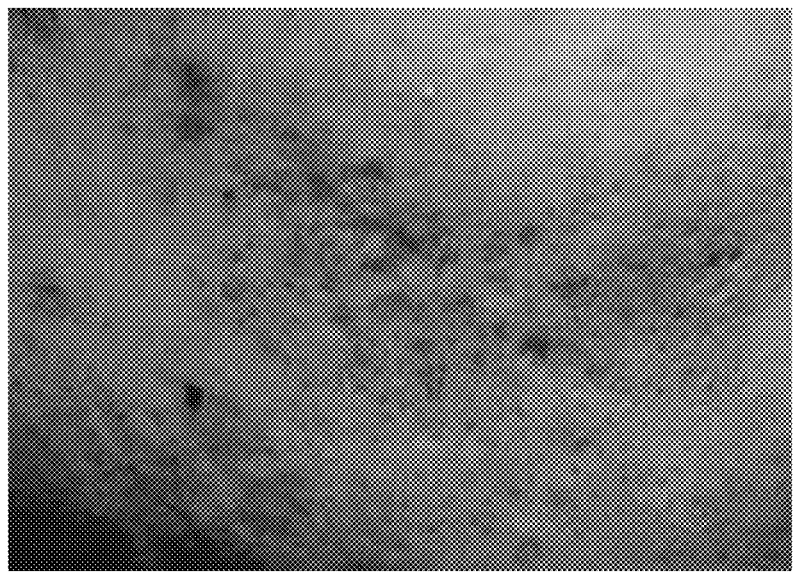
FIGS. 4A-4B are diagrams showing the comparison between before FIG. 4A and after one-day layered skin treatment FIG. 4B.
Figure 4B:
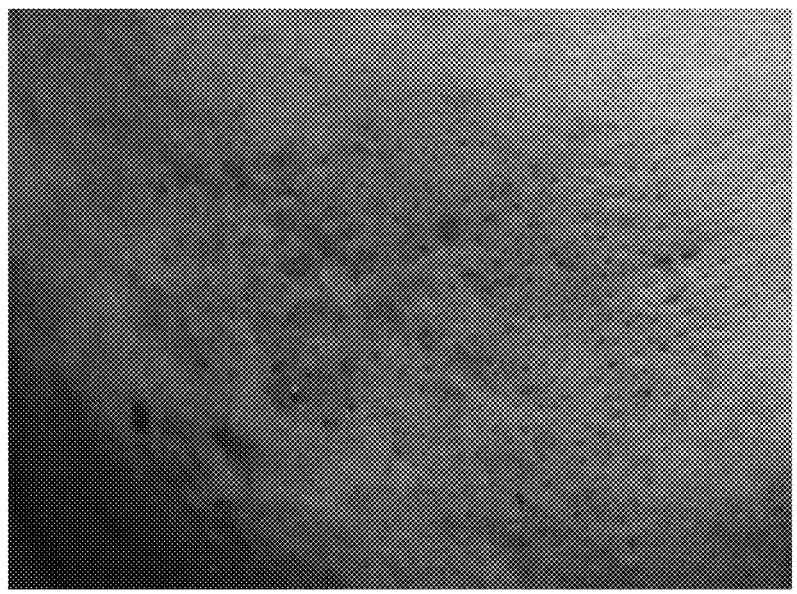
Figure 5A:
FIGS. 5A-5B are diagrams showing the comparison between before FIG. 5A and after one-day layered skin treatment after four months FIG. 5B.
Figure 5B:
Figure 6A:
FIGS. 6A-6B are diagrams showing the comparison between before FIG. 6A and after one-day layered skin treatment after one year FIG. 6B.
Figure 6B:
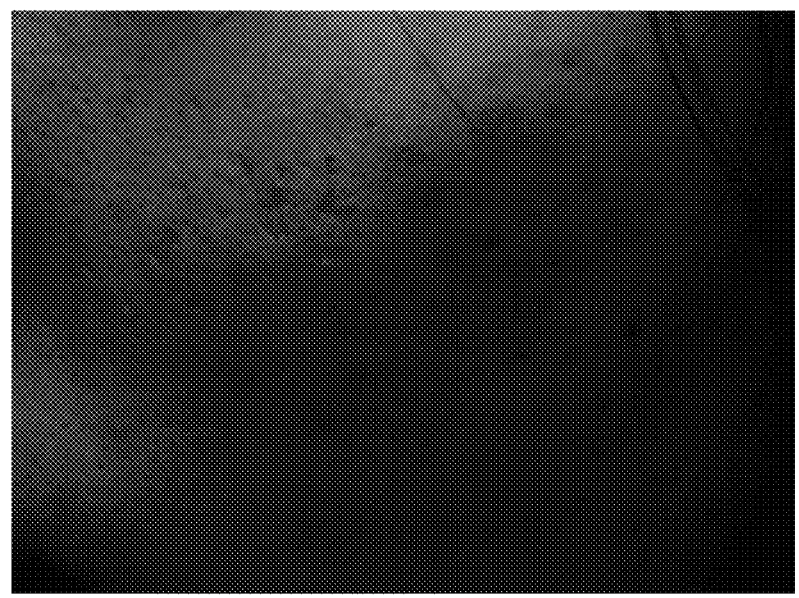

Both Deep Skin Layer Treatment and Superficial Skin Layer Treatment within One Day FIGS. 4, 5, and 6 depict the patient undergoing one-day treatment that include both layered skin treatment. The patient's deep skin layer is first treated with subcision, and then followed by superficial skin layer treatment with carbon dioxide Fraxel laser within the same day. FIG. 4A depicts pre-treatment skin (Grade 2-3). FIG. 4B depicts post-treatment skin (Grade 1-2). The result shows one-day layered treatment improves skin condition by 40-50%. FIG. 5A depicts treatment for Grade 2 skin condition. FIG. 5B depicts the same treatment after four months. The skin recovery rate remains the same at 40-50%. FIG. 6A depicts treatment for Grade 3 skin condition. FIG. 6B depicts treatment skin after one year. The result shows that the skin recovery rate remains the same at 40-50%.

Figure 7A:
FIGS. 7A-7B are diagrams showing the comparison between before FIG. 7A and after subcision, followed by carbon dioxide Fraxel laser treatment two weeks later FIG. 7B.
Figure 7B:
Figure 8A:
FIGS. 8A-8B are diagrams showing the comparison between before FIG. 8A and after carbon dioxide Fraxel laser treatment, followed by subcision two weeks later FIG. 8B.
Figure 8B:

FIGS. 7 and 8 depict the patient treated with two-stage layered treatment that is conducted weeks apart. In FIG. 7, patient's deep skin layer is first treated with subcision, and then the superficial skin layer is treated with carbon dioxide Fraxel laser two week later. FIG. 7A depicts pre-treatment skin. FIG. 7B depicts post-treatment skin. The result shows that two-stage layered treatment only improves skin condition by 20-30%. In FIG. 8, this shows the effect of reversing the order of layered skin treatment in which reverse the order of the two steps for skin layer treatment in which the superficial skin is first treated with carbon dioxide Fraxel laser and then deep skin layer is then treated with subcision two weeks later. FIG. 8A depicts pre-treatment skin. FIG. 8B depicts post-treatment skin. The two-stage layered treatment improves skin condition only by 10-20% if the order is reversed from claimed invention when the claimed invention improve the skin condition to 20-30%.

In summary, the results demonstrate that one-day treatment have better result than two-stage treatment that is conducted weeks apart. More importantly, data shows an improved and unexpected result when the deep layer treatment is performed first then followed by superficial layer treatment by using electromagnetic radiation and both treatment is performed within one day.

One skilled in the art will readily appreciate that the present invention is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of treating skin blemishes on a target skin area, consisting of:
   cutting fibrous bands at least 1 mm beneath said skin blemishes on the target skin area with a surgical subcision device;
   applying an electromagnetic radiation less than 1 mm beneath said target skin area within twenty-four hours from cutting said fibrous bands; and
   administering a substance onto said target skin area, wherein said substance is a growth factors, a collagen byproduct, a collagen precursor, a hyaluronic acid, a vitamin, an antioxidant, an amino acid, and a supplemental minerals, a platelet-rich plasma, a skin lightening medication and combination thereof;

wherein said electromagnetic radiation is provided by a group consisting of $CO_2$ laser, Fractional $CO_2$ laser, Erbium YAG Laser (Er: YAG laser), Fractional RF, 1550 nm Fraxel and any combination thereof; and wherein said electromagnetic radiation is transmitted at a transfer energy rate (r) of 0.0013 $J/cm^2$/second to 0.02 $J/cm^2$/second, with an energy density 2.5 $J/cm^2$ to 20 $J/cm^2$, and with an electromagnetic radiation wavelength 9400 nm to 111000 nm.

2. The method of claim 1, wherein said skin blemishes have a dermatological symptom selected from a group consisting of inflammatory skin condition, acne, skin aging, loose skin, irregular skin texture, enlarged pores, scars, pigment changes, wrinkles, skin atrophy, congenital skin defect and any combination thereof.

\* \* \* \* \*